(12) United States Patent
Saaski et al.

(10) Patent No.: US 10,690,660 B2
(45) Date of Patent: Jun. 23, 2020

(54) ENVIRONMENTAL SAMPLING AND ASSAY DEVICE

(71) Applicant: CBRN INTERNATIONAL, LTD, Dubai (AE)

(72) Inventors: Elric Saaski, Monroe, WA (US); Robert Fay Livingston, St. George, UT (US); Duane M. Fox, Snohomish, WA (US)

(73) Assignee: CBRN INTERNATIONAL, LTD., Dubai (AE)

( * ) Notice: Subject to any disclaimer, the term of this patent is extended or adjusted under 35 U.S.C. 154(b) by 0 days.

(21) Appl. No.: 16/211,744

(22) Filed: Dec. 6, 2018

(65) Prior Publication Data

US 2019/0107535 A1  Apr. 11, 2019

Related U.S. Application Data

(63) Continuation of application No. 15/708,073, filed on Sep. 18, 2017, now Pat. No. 10,197,558.

(Continued)

(51) Int. Cl.
*G01N 1/00* (2006.01)
*G01N 33/53* (2006.01)

(Continued)

(52) U.S. Cl.
CPC .............. *G01N 33/53* (2013.01); *C12M 1/34* (2013.01); *C12Q 1/04* (2013.01); *C12Q 1/70* (2013.01);

(Continued)

(58) Field of Classification Search
CPC ....................................................... G01N 1/00
See application file for complete search history.

(56) References Cited

U.S. PATENT DOCUMENTS 4,979,821 A  12/1990 Schutt et al.
5,209,903 A   5/1993 Kanamori
(Continued)

OTHER PUBLICATIONS

Genprime D-Cipher-151229, http://www.genprime.com/doa-test-reader.

(Continued)

*Primary Examiner* — Jyoti Nagpaul
(74) *Attorney, Agent, or Firm* — Timothy E. Spiegel Patent Law, PLLC; Timothy E. Spiegel

(57) ABSTRACT

An environmental sampling and assay system, utilizing coupons, and having an assay coupon wetting and monitoring assembly adapted to perform an assay on a coupon. The system also includes a coupon storage assembly and a coupon moving assembly, adapted to move a coupon from the coupon storage assembly to the coupon wetting and monitoring assembly. Further, the coupon storage assembly includes a first coupon magazine storing a set of first-shaped coupons and a second coupon magazine storing a set of second-shaped coupons, different in shape from the first-shaped coupons, and wherein the coupon moving assembly includes a first moveable coupon carrier, positioned to receive coupons from the first magazine, that is shaped to hold first-shaped coupons and a second moveable coupon carrier, positioned to receive coupons from the second magazine and that is shaped to hold second-shaped coupons.

7 Claims, 8 Drawing Sheets

Related U.S. Application Data

(60) Provisional application No. 62/395,596, filed on Sep. 16, 2016.

(51) Int. Cl.
*G01N 1/22* (2006.01)
*C12M 1/34* (2006.01)
*C12Q 1/04* (2006.01)
*C12Q 1/70* (2006.01)
*G01N 35/00* (2006.01)
*G01N 1/38* (2006.01)
*G01N 1/26* (2006.01)
*G01N 1/02* (2006.01)

(52) U.S. Cl.
CPC ............ *G01N 1/2273* (2013.01); *G01N 1/38* (2013.01); *G01N 35/00029* (2013.01); *G01N 1/26* (2013.01); *G01N 2001/022* (2013.01); *G01N 2035/00089* (2013.01); *G01N 2035/00148* (2013.01); *G01N 2035/00891* (2013.01)

(56) References Cited

U.S. PATENT DOCUMENTS

| | | |
|---|---|---|
| 5,538,691 A | 7/1996 | Tosa et al. |
| 6,136,611 A | 10/2000 | Saaski |
| 6,615,763 B2 | 9/2003 | Edwards |
| 6,639,663 B1 | 10/2003 | Markle et al. |
| 6,910,445 B1 * | 6/2005 | Manthei .......... A61D 7/04 119/420 |
| 7,651,869 B2 | 1/2010 | Saaski |
| 7,678,338 B2 | 3/2010 | Sleeper |
| 8,131,477 B2 | 3/2012 | Li et al. |
| 8,411,916 B2 | 4/2013 | Hsieh et al. |
| 8,583,379 B2 | 11/2013 | Li et al. |
| 8,698,881 B2 | 4/2014 | Fleming et al. |
| 8,824,800 B2 | 9/2014 | Bremnes et al. |
| 8,865,089 B2 | 10/2014 | Blatt et al. |
| 8,889,424 B2 | 11/2014 | Ehrenkranz et al. |
| 8,916,390 B2 | 12/2014 | Ozcan et al. |
| 9,241,663 B2 | 1/2016 | Jena et al. |
| 9,386,221 B2 | 7/2016 | Kauniskangas et al. |
| 9,390,237 B2 | 7/2016 | Myers et al. |
| 9,600,878 B2 | 3/2017 | Tsai et al. |
| 10,197,558 B1 | 2/2019 | Saaski |
| 2008/0304723 A1 | 12/2008 | Hsieh et al. |
| 2010/0304658 A1 * | 12/2010 | Grcevic .......... B60P 3/005 454/187 |
| 2013/0280698 A1 | 10/2013 | Propper et al. |
| 2014/0065647 A1 | 3/2014 | Mamenta |
| 2015/0056719 A1 | 2/2015 | Karlovac et al. |
| 2016/0080548 A1 | 3/2016 | Erickson et al. |
| 2016/0131592 A1 | 5/2016 | Cooper |
| 2017/0300779 A1 | 10/2017 | Saaski |

OTHER PUBLICATIONS

Guardian Reader Manual, Alexeter Technologies, LLC, Wheeling, IL.
NIDS® Stand-Alone Reader III User Manual, Smiths Detection, Inc., Danbury, CT.
Tetracore Biothreat Alert Reader; http://www.tetracore.com/biowarfare/index.html.
Chemring, Joint Biological Point Detection Systems Overview, Apr. 9, 2003, http://www.chemringds.com/products/biological-detection/jbpds.aspx.

\* cited by examiner

FIG. 2A

ENVIRONMENTAL SAMPLING AND ASSAY DEVICE

RELATED APPLICATIONS

This application is a continuation of Ser. No. 15/708,073 filed on Sep. 18, 2017, and claims benefit of provisional application U.S. Ser. No. 62/395,596 filed on Sep. 16, 2016 which are incorporated by reference as is fully set forth herein.

BACKGROUND

There is an ongoing concern about the possibility of biological or chemical substances being released into the air with the intent to harm people in the release area. Rapid detection of harmful substances is very helpful in meeting this threat, by speeding evacuation, inoculation, or the administration of an antidote. To meet this threat, with respect to biological substances, the Joint Biological Point Detections System (JBPDS) has been developed. This system includes an initial sensor that constantly monitors the air, and which triggers an assay test for biological substances, when some warning condition is encountered. Unfortunately, the JBPDS is bulky, and requires cooling and heating, making the entire system even bulkier. Because of these factors, it has not been packaged in a form that protects users from contamination. Moreover, only one size and shape of assay coupon or strip can be accepted into the JBPDS, blocking the use of many commercially available assay strips. Further, the assay reader does not check to determine that the assay strip has been properly wetted before the time period for an assay-read has elapsed, so that the full assay time period must elapse before a botched test can be detected. As noted, the JBPDS is configured to only detect biological, as opposed to chemical threats. Accordingly, the use of the JBPDS is hampered by a rigid requirement for assay coupons that fit a predetermined geometry and that must be read in a predetermined manner. Personnel using the JBPDS are exposed to the biological substances, for which the JBPDS is testing.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect, the present invention may take the form of an environmental sampling and assay system, utilizing coupons for detecting target substances, and that includes a data input assembly; an environment sampling assembly, the sampling assembly mixing an environmental sample with a liquid to create a sample liquid, bearing the environmental sample; a coupon wetting assembly, positioned to wet coupons with the sample liquid; a coupon perceiving device; a coupon storage assembly, including stored coupons; a coupon moving assembly; and a data processing and control assembly, communicatively coupled to the coupon storage assembly, sampling assembly, wetting assembly, moving assembly and coupon perceiving device. The data processing and control assembly controls the coupon storage, sampling, wetting and moving assemblies and the coupon perceiving device to form an environmental sample and produce an environmental sample infused sample liquid, move coupons from the storage assembly to the wetting assembly; wet coupons with the sample liquid; move the coupon from the wetting assembly to a position substantially optimized for viewing by the coupon perceiving device, and form coupon perceptions; and process the coupon perceptions and produce an advisory signal in response to the processing. The system also includes a human perceptible advisory issuing device, which issues advisories based on the advisory signal. Further, the stored coupons include coupons of a first coupon type, adapted to detect at least a first substance, and coupons of a second coupon type, adapted to detect at least a second substance distinct from the first substance, and wherein the data processing and control assembly commands the coupon moving assembly to pick and move a coupon of the first coupon type or the second coupon type, depending on input received through the data input assembly.

In a second separate aspect, the present invention may take the form of an environment sampling and substance detection vehicle, having a vehicle that defines an interior space, into which filtered air is pumped, thereby creating positive air flow out of the interior space, and preventing the entry of unfiltered air into the interior space. A glove box located in the interior space, and which has a sample collection port to the outside. Finally, a substance detection coupon reading system is located in the glove-box.

In a third separate aspect, the present invention may take the form of an environment sampling and assay system, utilizing coupons, and having an assay coupon wetting and monitoring assembly adapted to perform an assay on a coupon. The system also includes a coupon storage assembly and a coupon moving assembly, adapted to move a coupon from the coupon storage assembly to the coupon wetting and monitoring assembly. Further, the coupon storage assembly includes a first coupon magazine storing a set of first-shaped coupons and a second coupon magazine storing a set of second-shaped coupons, different in shape from the first-shaped coupons, and wherein the coupon moving assembly includes a first moveable coupon carrier, positioned to receive coupons from the first magazine, that is shaped to hold first-shaped coupons and a second moveable coupon carrier, positioned to receive coupons from the second magazine and that is shaped to hold second-shaped coupons.

In a fourth separate aspect, the present invention may take the form of an environmental sampling and assay system, utilizing coupons, and having an environment sampling assembly, the sampling assembly mixing an environmental sample with a liquid to create a sample-liquid, bearing environmental substances. Further, a coupon wetting assembly is positioned to wet coupons located at a wetting position with the sample-liquid and the system includes a coupon perceiving device. Also, a coupon storage assembly includes stored coupons, with each coupon adapted to detect at least a first target substance in a manufacturer specified coupon development time, when the target substance is present in a concentration above a threshold. Additionally, there is a coupon moving assembly. A data processing and control assembly is communicatively coupled to the sampling coupon storage assembly, sampling assembly, wetting assembly, moving assembly and coupon perceiving device, and controls the coupon storage assembly, sampling, wetting and moving assemblies and the coupon perceiving device, to form an environmental sample and produce an environmental sample infused sample liquid; move coupons from the storage assembly to the moving assembly and further to the wetting position; wet the coupons with the sample liquid; move the coupon from the wetting assembly to a position substantially optimized for viewing by the coupon perceiving device, and form coupon perceptions, respectively; and process coupon perceptions from the coupon perception device to form a detection if a target substance is present and produce an advisory signal in response to the processing. Further, a human perceptible advisory issuing device issues an advisory based on the advisory signal. Finally, the data process and control assembly coupon storage assembly begins to receive and process images from the coupon perceiving device before the manufacturer coupon development time has elapsed, after coupon wetting.

In addition to the exemplary aspects and embodiments described above, further aspects and embodiments will become apparent by reference to the drawings and by study of the following detailed descriptions.

BRIEF DESCRIPTION OF THE DRAWINGS

FIG. 2a is a multichannel biological assay coupon showing the strong presence of one targeted pathogen.

DETAILED DESCRIPTION OF THE PREFERRED EMBODIMENTS

Figure 1A:
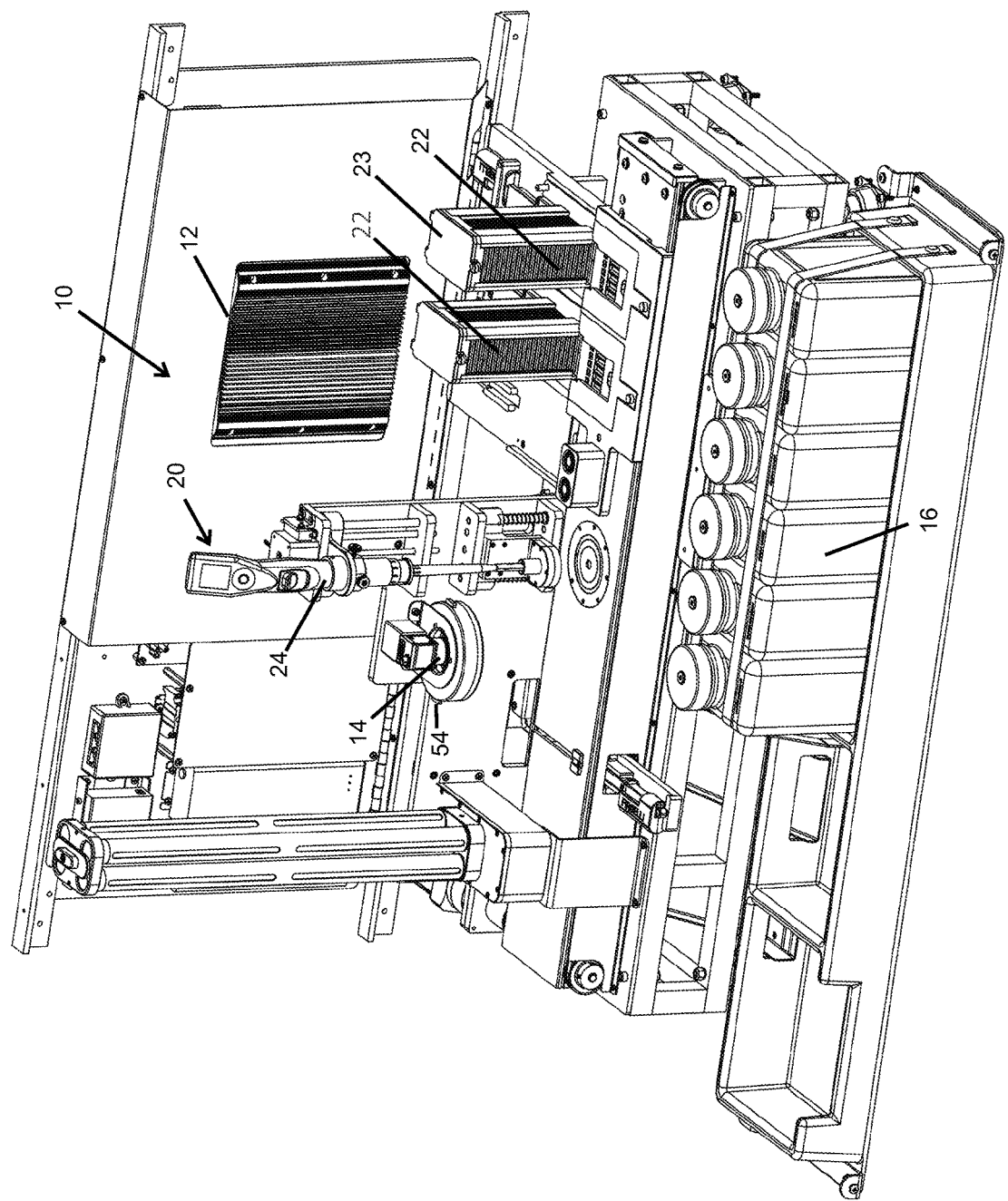
FIG. 1a is a front isometric view of an environmental sampling and assay device, according to the present invention.
Figure 1B:
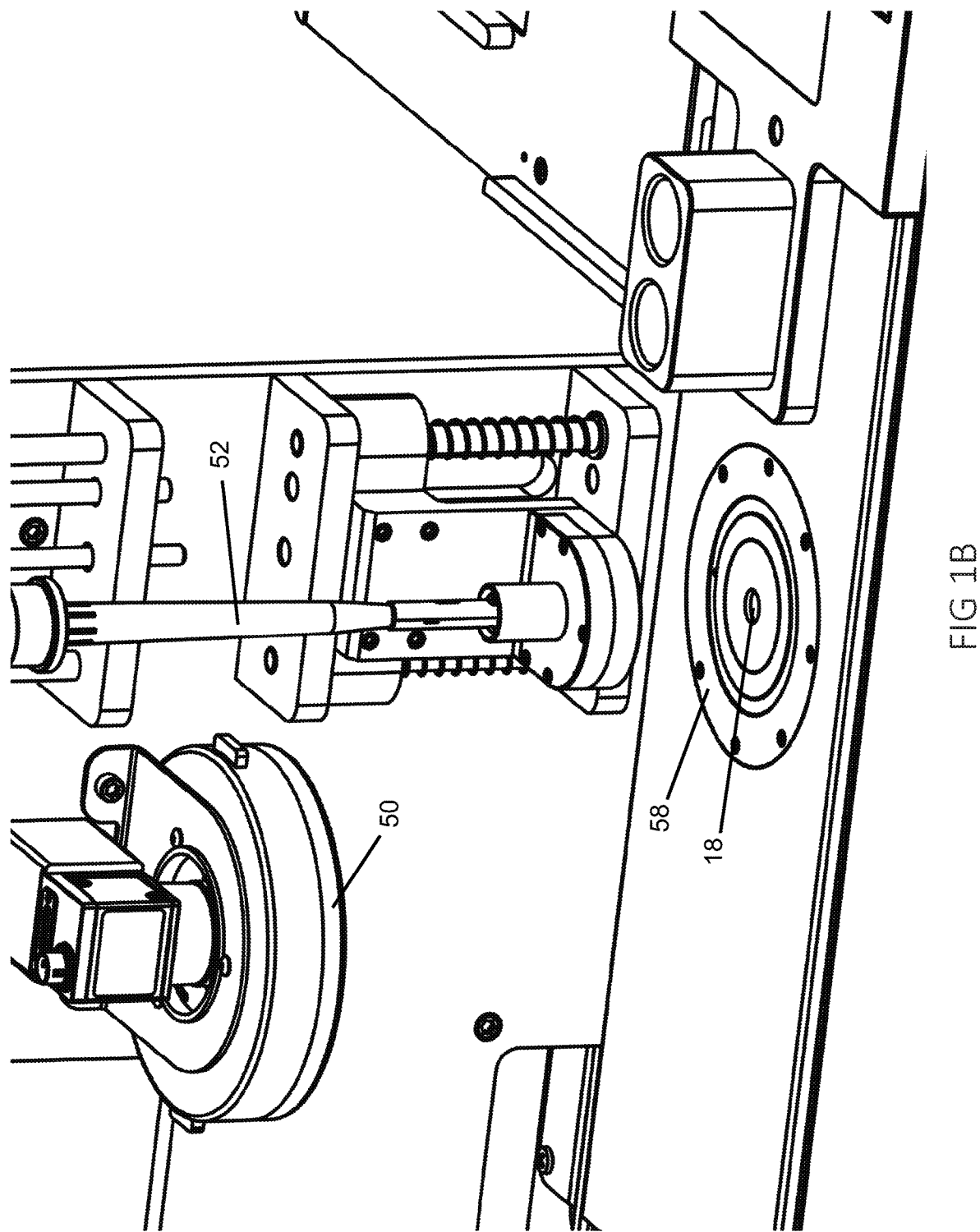
FIG. 1b is a detail view of FIG. 1, from the same perspective, showing the wetting assembly.

Definition: In this application the word, "substance" may refer to an organism, such as a microbe.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 3:
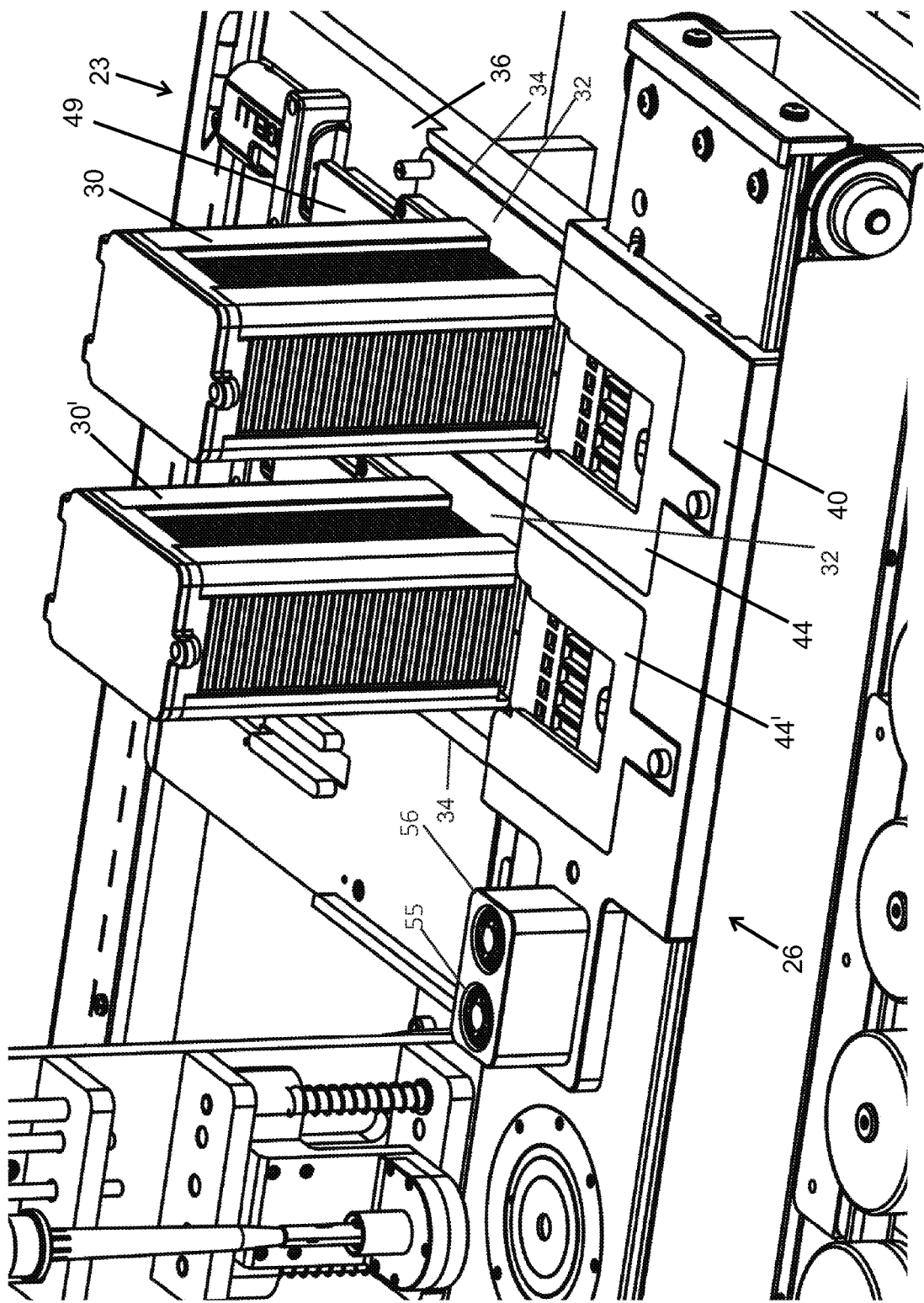
FIG. 3 is a detail view of FIG. 1, from the same perspective, showing the coupon storage assembly and coupon moving assembly.
Figure 4:
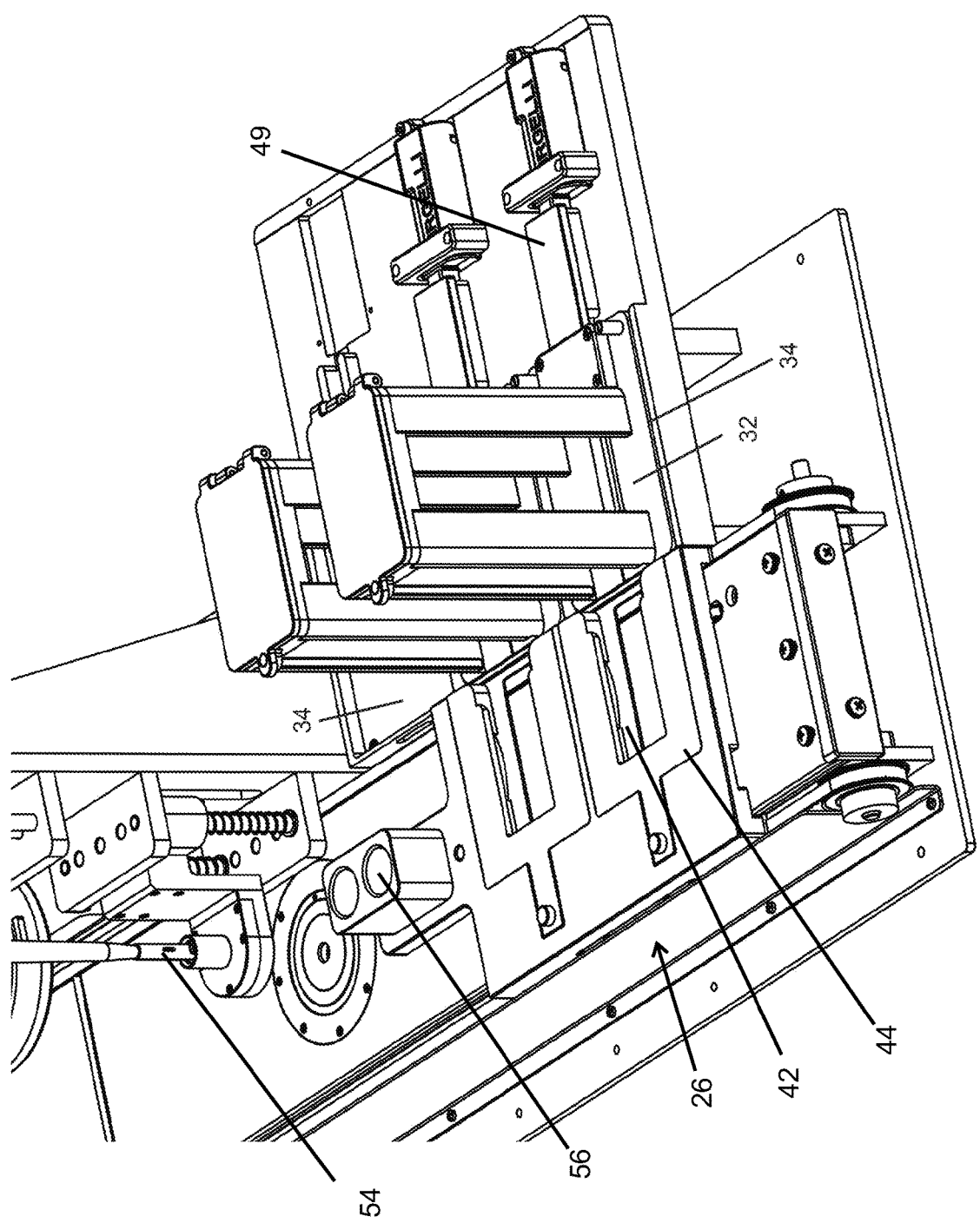
FIG. 4 is a detail view of the device of FIG. 1, from a rotated perspective, showing further features of the coupon storage assembly.
Figure 5:
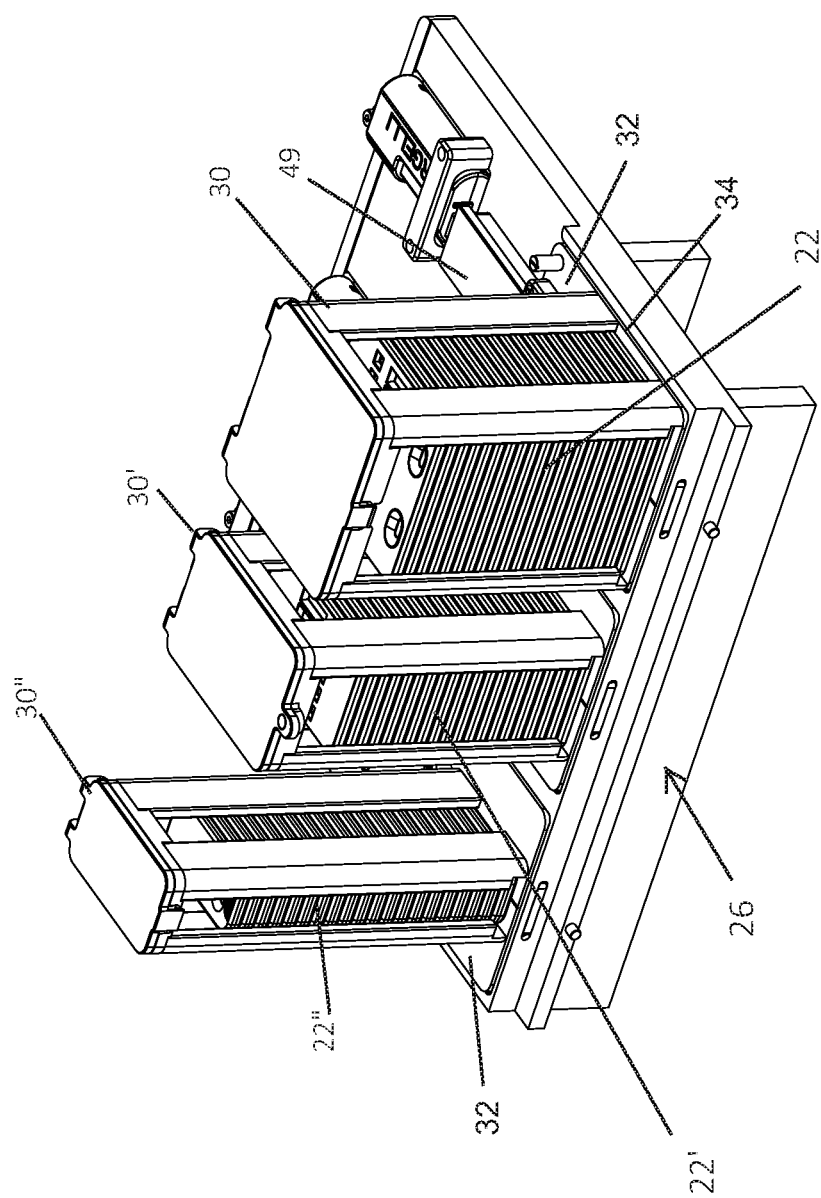
FIG. 5 is a partial view of the device of FIG. 1 placed into a different configuration in which coupon magazines having differing dimensions hold coupons having differing dimensions.

In broad overview, referring to FIGS. 1a, 1b, 3 and 6 in a preferred embodiment of an environmental sampling and assay formation system 10, a data processing and control assembly 12, controls the various elements of the system 10, to be detailed below, and processes imagery formed by a coupon perceiving device, such as a digital camera 14, to determine possible presence of biological or chemical contaminants, as will also be described further, below. After a detection cycle is triggered by input received over a data input assembly 68, from a preliminary detection system 70 (FIG. 6), an environmental sample (air, water or solid) is mixed with buffer from bottles 16 to form a sample liquid bearing environmental substances held in a sample cup 18 (FIG. 3). Bottles 16 also hold deionized water, bleach, and waste, which may also be mixed with a sample. A pipetting assembly 20 (which may also be referred to as a wetting assembly) withdraws sample liquid from the sample cup 18 and delivers sample liquid to coupons 22 (sometimes also referred to as "tickets" in the industry) that are brought from a storage assembly 23, to a wetting position directly below the pipette 24 by the coupon movement assembly 26 (FIGS. 3-5). Movement assembly 26 then moves the coupons 22 to a position under the camera 14, and coupon perceptions, such as digital images, are formed at least every minute, with assembly 12 analyzing these coupon perceptions to detect a coupon indication of the presence of a target substance. A human-perceptible advisory issuing device issues a signal at any point that such an indication is detected. The advisory may include a visual or auditory cue.

Figure 6:
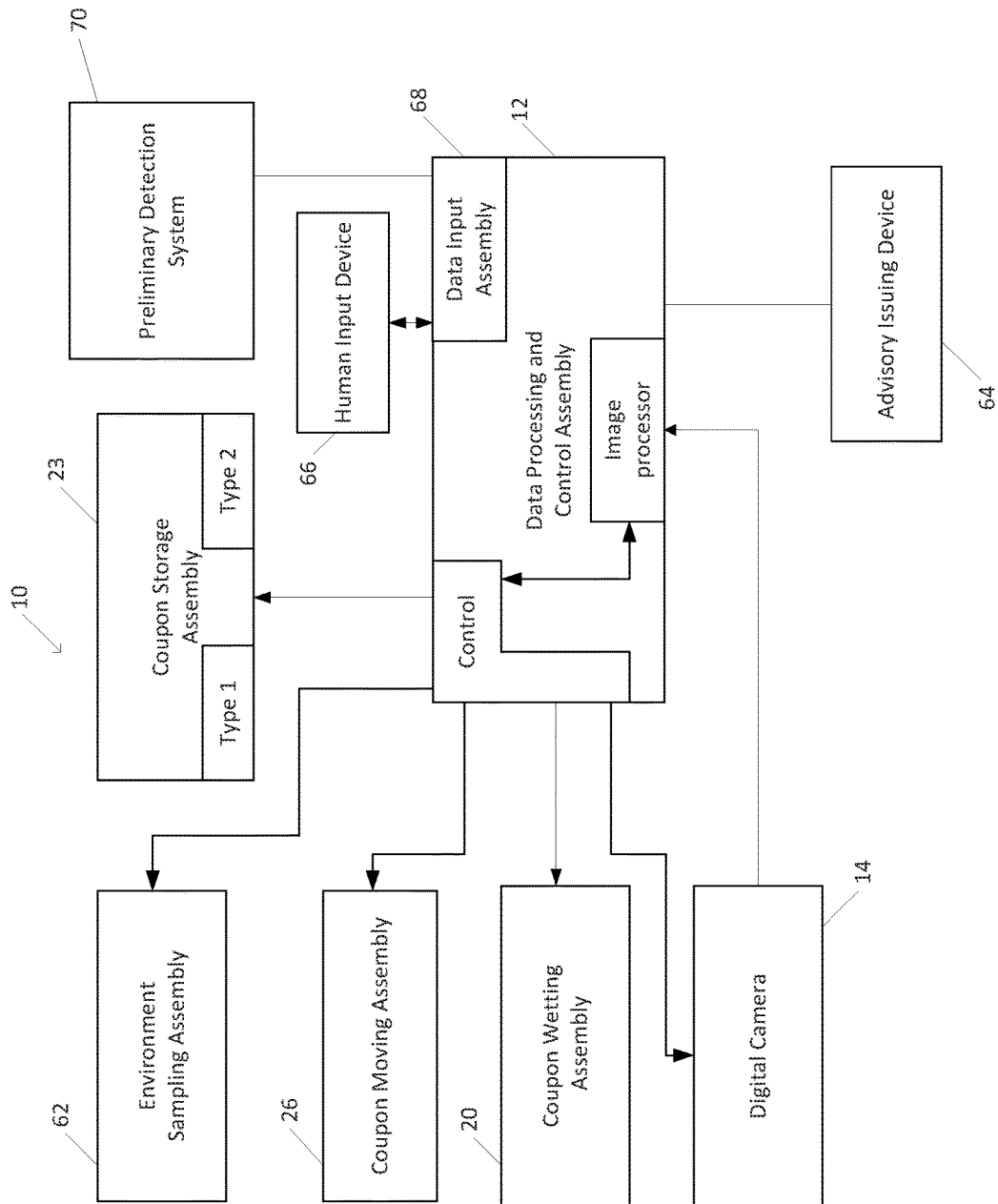
FIG. 6 is a block diagram, of the environmental sampling and assay device of FIG. 1, showing the communications connections between different parts of the device.

A number of manufacturers produce coupons having various shapes and sizes and designed to detect various differing biological substances. Some coupons 22 include an array of detection areas, one for each of as many as 8 different pathogens, or more. Much of this technology is proprietary, so that for many biological substances of concern there is only one coupon size (and shape) available that can be used to test for the substance. Accordingly, there is no single coupon size that could be used to detect all biologic substances of concern. Consequently, in order to detect the broadest possible range of biological substances, different sized coupons must be accepted. Referring to FIGS. 5 and 6, to meet this need, storage assembly 23 includes differently shaped coupon magazines 30 provided as part of system 10. Each of the magazines 30, however, has a standard shaped base 32 (FIG. 3), that is adapted to fit into a standard sized opening 34 (shown empty of magazine 30, in FIG. 3) in a support plate 36, thereby permitting a user to exchange first magazine 30, accommodating a stack of first sized coupons 22, for different magazines 30' and 30", that accommodate different sizes of coupon 22' and 22". Standard sized base 32 and standard sized opening 34 are mating features that permit any size magazine, having the standard sized base 32 to attach to storage assembly 23 at a standard sized opening 34 (also a mating feature). Other mating features that achieve the same purpose, for example matching posts and sockets, could serve the same function. Referring to FIG. 3, in like manner, a coupon carriage 40 has standard sized openings 42 (FIG. 4), in which can fit a first coupon carrier 44, holding first sized coupon 22, or a second coupon carrier 44' adapted to hold the second sized coupon 22', and third sized coupon 22" (FIG. 5). Although magazines 30 and 30' and carrier 44 and 44' appear to be the same in FIG. 3, they may in fact be different, to accommodate the different magazines 30, 30' and 30" and coupons 22, 22' and 22" shown in FIG. 5. Coupons 22 are stacked along their dimension of least extent to permit the greatest number of coupons 22 to be stored in the magazines 30.

Once system 10 has been configured and is ready to operate, when an indication is received from the preliminary detection system 70, coupons 22 that are in a load position at the bottom of the magazine 30 are loaded by linear actuator mechanisms 49, (which are also a part of storage assembly 23) from magazines 30 into carriers 44. Gravity causes the next coupon 22 in each magazine 30 to descend into the load position from which it can be delivered to a carrier 44, next. Coupons 22 are then moved to a position beneath camera 14 to check for correct coupon 22 loading. If this test is passed, pipette assembly 20, which includes an electronic pipette 24 (controlled by assembly 12), having a disposable reservoir 52 and needle (not shown), extending downwardly from the end of reservoir 52, takes up to 5 cc's of sample liquid from the sample cup 18, and uses this to fill the coupon reservoirs 52 for coupons 22. After this filling, the coupons 22 are, for the first few minutes, checked by camera 14 every 30 seconds to verify proper wetting of the coupon 22, typically by checking to confirm that the control pattern is beginning to appear. If this is not achieved, the test may be aborted, and restarted, depending on which coupon 22 was not properly wetted and the logic programming of assembly 12. Alternatively, a human operator is informed and makes the decision to continue or restart. If the test continues (as it generally will) the coupons 22 are placed under camera 14 once every minute (illuminated by a light or flash ring 50), thereby providing enough slack time to fill two sample vials 55 held in carrier 56.

Many coupons 22 include a control pattern (typically a stripe) that develops when wetted, even in the absence of a target substance, for purposes of comparison. In a preferred embodiment, this pattern is read by digital camera 14 and used in comparison with the pattern that develops only in the presence of the target substance, in order to form a detection. It is, however, not entirely necessary to compare the test pattern with the control pattern, as in another preferred embodiment, a digitized target pattern (an image of a developed coupon) is introduced into the memory of assembly 12. This data entry may be performed by placing a developed coupon 22 or a control section into system 10 during system configuration and using a user interface (not shown) to command system 10 to use a digital camera 14 to take a digital photograph of the developed coupon 22 and store it in memory, properly labeled as a digitized image of a target pattern. In another preferred embodiment, system 10 is provided with digitized target images already stored. Otherwise digitized target images may be introduced into system 10 by way of the data input assembly 68.

Figure 2A:
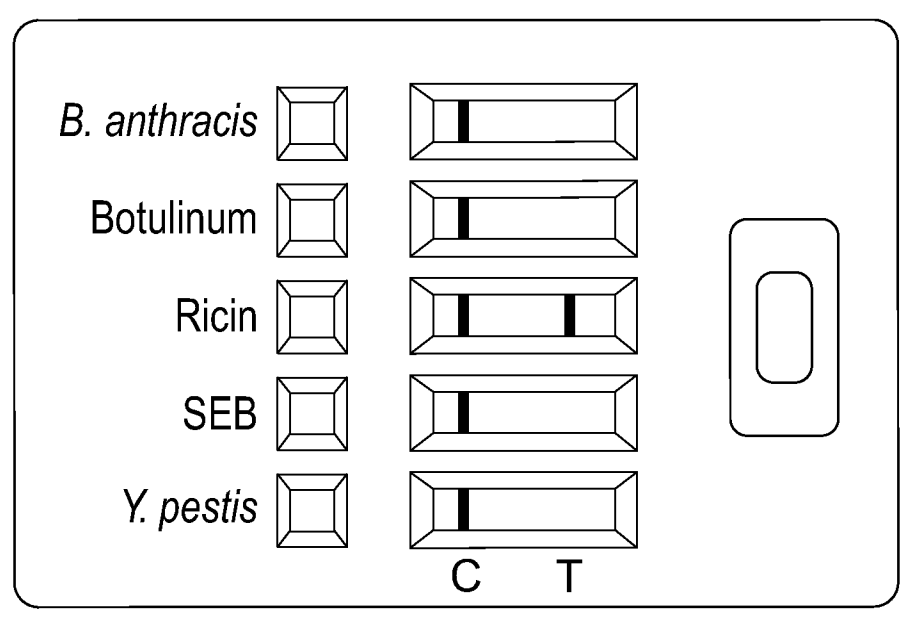
Figure 2B:
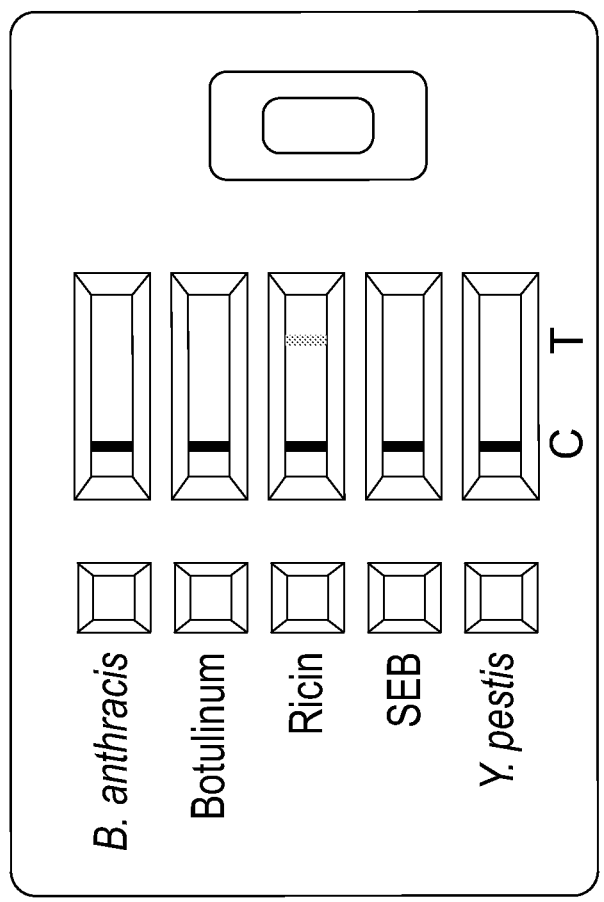
FIG. 2b is a multichannel biological assay coupon showing the weak presence of the aforementioned targeted pathogen, or an early indication of the targeted pathogen.

Assembly 12 compares each image with the digitized target image stored in its memory, or with the control pattern as perceived by the digital camera 14. Although coupon manufacturers specify a development time that is typically permitted to elapse before a human user reads the coupon 22, in a preferred embodiment, coupon 22 examination by camera 14 and data processor 12 begins long before this time period has elapsed, with a target substance detection also determined minutes before the development time has passed. In one embodiment, if the target substance is at a concentration that is at least 20% above the minimum level that can be detected by the coupon 22 after the full manufacturers' specified coupon 22 development time has passed, the system provides an advisory signal prior to the passage of the full manufacturers' specified development time. This provides human operators with a quicker result that could in some circumstances be very important. In one embodiment, each pixel is compared with a threshold that is one-tenth of the intensity of the fully developed target pattern (dark if the developed target pattern is dark and light if the developed target pattern is light) if 95% of the pixels in the target pattern area pass this threshold and less than 5% of the pixels outside of the target area pass this threshold, then a detection is determined and a human perceptible indication, such as an auditory signal and/or visual signal is provided, to alert any nearby people that the target substance has been detected. Many other algorithms, including least squares detection and various linear algorithms are used in alternative embodiments. FIG. 2a is an illustration of a test pattern, and FIG. 2b is an illustration of a partially developed coupon 22, showing an indication of the test pattern of FIG. 2a. In one preferred embodiment, a coupon test pattern developed to the contrast level shown in FIG. 2b is sufficient to trigger an alarm.

The use of digital camera 14 provides a much greater flexibility of use, compared with some prior art systems in which a less robust reader has been used. In a preferred embodiment, assembly 12 is programmed to detect the change in hue that chemical detecting coupons present as an indication of the detection of a chemical substance. Also, carriers 44 are provided that can accept the size and shape of chemical coupons.

In one preferred embodiment, system 10 is housed in a vehicle interior that is essentially closed to the outside world and with positive air pressure (from air forced in from the outside and thoroughly filtered, on route) causing constant air flow from inside the vehicle interior to the outside through residual leaks, if any, thereby blocking airborne biological substances from entering the work area. System 10 is housed in a "glove-box," a largely transparent, air tight box, having air-tight gloves sealed to apertures leading through the box walls. Ports lead from the glove-box to the outside, to permit the gathering of air samples. Accordingly, a safe work space is created for users of system 10.

The enclosure of the system 10 in an air-tight glove box is not limited to its use in a vehicle, but is used in many embodiments as it bears the advantage of protecting test personnel from potential hazards in the samples, a feature not usually provided in the prior art. One reason that prior art systems do not typically afford this level of protection to test personnel is that an air tight enclosure may result in the buildup of water vapor in the glove box due to the handling of water borne samples. Such handling inevitably leads to evaporation of water into the closed glove box volume, creating a risk that water condensation onto optics or electronics may occur with deleterious effects on operation. In a preferred embodiment, the humidity is monitored by assembly 12 and a dehumidifier is turned on as needed to create an optimal or at least not dangerous, humidity level. Due to a desire to maximize operational time and minimize equipment failures, a solid-state dehumidifier using a thermoelectric module and free convection heat transfer is preferred, eliminating the need for a compressor or air moving fan. Dehumidifiers of this type are described at www.myivation.com and are available from Amazon.com under the Ivation trademark.

In another preferred embodiment, sample cup 18 is sterilized by exposure to ultraviolet light from four LEDs (not shown), which are part of UV-C sterilization system 58. The system 58 is positioned such that both the sample cup 18 and the tops of bottles 16 are sterilized using an intensity of about 96 mW/cm$^2$ at 280 nm for 5-20 seconds.

Referring, now, to FIG. 6, system 10 includes the previously noted data processing and control assembly 12, that controls the digital camera 14, the coupon wetting system 20, the coupon storage assembly 23 and the coupon moving assembly 26 to select a coupon 22, which is then wetted and moved to a position where the digital camera 14, in conjunction with data processing assembly 12, can monitor its development. Prior to these actions, however, an environment sampling system 62 must form a liquid sample from ambient air, or from a liquid that is accessible by system 10, or even from a solid sample, said liquid sample being then entered into a sample cup 18 from which the wetting assembly 20 draws liquid (using a pipette 24), and uses it to wet a coupon 22. If a target substance (or pathogen) is detected, then an advisory issuing device 64, which could be an auditory or visual announcement system, or both, is used to let an operator know that this has happened. A human input device 66 can be used by a human operator to command a particular test cycle. In one embodiment, device 66 is a laptop, tablet or other form of computer that connects with the rest of system 10 either through a USB port, ethernet port (which in a preferred embodiment is fiberoptic), or a wireless connection such as an RF connection, which may conform to either a Bluetooth or WIFI protocol. In another embodiment, device 66 is a custom-made input device, having a keypad and display. In some embodiments, there is overlap between input device 66 and advisory issuing device 64, with the display screen of device 66 used for the issuance of advisories. In yet another embodiment, as noted above, the preliminary detection system 70, for example an aerosol particle and bioluminescence detector such as the TacBio trigger developed by the US Army, is connected to the data input assembly 68 of system 10 and is able to command system 10 to begin a test of a particular type when an aerosol quality is found that meets a set of criteria. For example. when a biological particle count above a specified level is found, or if the particles have luminescent properties that fit in a prespecified range. The preliminary detection system 70 is fed by an aerosol sampler or aerosol concentrator. In one embodiment, the aerosol concentrator has an air throughput of 4,000 liters per minute and extracts aerosol particles from sampled air and injects them into a secondary circuit flowing at a much slower rate that is compatible with devices used for creating liquid samples. Environment sampling system 62 taps into this flowing aerosol concentrate with a 300 liter per minute cyclone wet sampler, to prepare a liquid sample for coupon wetting.

All of the assemblies noted in the discussion above have varying embodiments not specifically mentioned. In an alternative embodiment, the coupon wetting assembly 20 wets the coupons 22 by way of small disposable sponges. The coupon moving assembly 26 makes use of small electric vehicles that are optically guided. The coupon storing assembly 23 stores coupons 22 on turntables. Moreover, it should be noted that there are many forms of digital cameras, including linear cameras that simply scan back and forth with one line of pixels, two dimensional digital cameras and video cameras 14, all of which are perceiving devices. In a preferred embodiment, the perceiving device is a fiber optic cable, that is connected to a charge coupled device at the processing and control assembly 12. In a preferred embodiment, processing and control assembly 12 includes one or more digital computers, which may be in the form of a microcontroller and/or microprocessor, of digital signal processing chip or chips. In a preferred embodiment, processing and control assembly 12 includes non-transitory computer readable memory that has a program that controls the remainder of system 10 to perform the tasks disclosed and claimed herein. Assembly 12, in embodiments, also includes analog-to-digital convertors and digital-to-analog convertors and amplifiers, sufficient to produce control signals for controlling the various systems described.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. An environmental sampling and assay system, comprising:
   (a) a sealed glove box having a sample collection port to the outside;
   (b) a humidity sensor and a dehumidifier, located in said glove box, said dehumidifier controlled by said humidity sensor to prevent humidity in said glove box from rising above a threshold level;
   (c) a set of coupons; and
   (d) a substance detection coupon reading system, located in said glove box and capable to gather a sample from said sample collection port, form a liquid that includes said sample, select a first coupon from said set of coupons, wet said first coupon with said liquid, read said first coupon and provide a human operator with information from said first coupon.

2. The system of claim 1, wherein said dehumidifier is a solid state dehumidifier.

3. The system of claim 1, further being located within a vehicle having an opening to permit said sample collection port to access air outside of said vehicle.

4. The system of claim 3, wherein said vehicle further includes an air pressure system that maintains a higher level inside said vehicle than outside said vehicle, as an additional guard against contaminants entering said vehicle.

5. The system of claim 1, wherein said set of coupons includes coupons both for detection of substances and coupons for detection of chemical substances, so that said substance detection coupon reading system can detect both biological and chemical substances.

6. The system of claim 1, wherein said set of coupons includes a first set of coupons having a first size and a second set of coupons having a second size.

7. The system of claim 1, further capable to perform the sequence of actions in paragraph (d) automatically.

* * * * *